United States Patent [19]
Miller

[11] 3,986,495
[45] Oct. 19, 1976

[54] OPTICALLY EXCITED DIODE CURRENT LIMITER

[75] Inventor: James L. Miller, Westford, Mass.

[73] Assignee: Hewlett-Packard Company, Palo Alto, Calif.

[22] Filed: Nov. 3, 1975

[21] Appl. No.: 628,691

[52] U.S. Cl. .......... 128/2.1 P; 128/2.06 B; 307/311; 317/33 R; 323/9; 328/2
[51] Int. Cl.² .......... A61B 5/00
[58] Field of Search .......... 128/2.1 P, 2.1 A, 2.06 B; 307/202 R, 237, 264, 311, 92; 317/33 R; 328/2, 169; 323/9

[56] References Cited
UNITED STATES PATENTS

| | | | |
|---|---|---|---|
| 3,099,799 | 7/1963 | Bahrs et al. | 128/2.1 P |
| 3,348,064 | 10/1967 | Powlus | 307/311 |
| 3,418,480 | 12/1968 | Miller | 307/311 |
| 3,521,087 | 7/1970 | Lombardi | 128/2.1 P |
| 3,593,038 | 7/1971 | Cavallius et al. | 328/2 |
| 3,605,728 | 9/1971 | Ogle | 128/2.1 P |

Primary Examiner—William E. Kamm
Attorney, Agent, or Firm—Stephen P. Fox; Robert S. Hulse

[57] ABSTRACT

An optically excited diode current limiter, when placed in series with a lead having an electrode attached to a patient such as an EKG or EEG lead, conducts physiological signals picked up by the electrode and protects the patient from electrical shock by limiting the amount of current flowing through the lead.

4 Claims, 3 Drawing Figures

OPTICALLY EXCITED DIODE CURRENT LIMITER

BACKGROUND OF THE INVENTION

Whenever an electrode at the end of an EKG or EEG lead is applied to a patient's body, a potential electrical shock hazard to the patient is created. Electrodes are generally designed to provide a low resistance connection to the patient so as to facilitate the detection of low amplitude physiological signals from the patient's body. However, this low resistance connection also facilitates the application of hazardous voltages to the patient and the flow of current to and from the patient, thereby exposing the patient to electrical shock. Hazardous voltages and currents may arise from static discharges, from contact of the patient or of an electrode with surrounding electrical equipment, from EKG or EEG equipment failure, from ground loops, or from stray capacitance which often develops between the lead and grounded objects to which the lead is coupled.

Many voltage and current limiting devices such as isolator circuits and non-linear series circuits have been developed to protect the patient from electrical shock. Isolator circuits generally comprise considerable floating or non-grounded circuitry, including modulators and transducers or couplers of the optical, magnetic, electric field or acoustic type. However, these circuits are usually complex and costly, and because these circuits are usually incorporated into biomedical equipment located away from the patient, they do not adequately protect the patient from electrical shock such as from long-lead shunt currents that arise from stray capacitance in the lead. Also, isolator circuits do not adequately eliminate artifacts that sometimes reside in the physiological signal received from the patient. Such artifacts are often caused by large electrostatic common mode voltages arising from multiple electrodes placed on the patient's body.

Non-linear series circuits also have certain inherent disadvantages which cause them to provide inadequate shock protection to the patient. These disadvantages are described below. Most known non-linear series circuits are semiconductor circuits using Field Effect Transistors (FET), Bipolar Transistors, or Diodes.

FET circuits are unduly complex and costly and can be damaged easily when large overload voltages are applied such as electrocautery and defibrillation voltages thereby providing inadequate patient protection. Electrocautery voltages are generally about 2 kilovolts in magnitude while defibrillation voltages are generally about 8 kilovolts in magnitude.

Bipolar transistor circuits, which are often constructed having a plurality of bipolar transistors, a battery, and one or more resistors, have the same disadvantages as FET circuits mentioned above plus the added disadvantage of limited battery life.

Diode type current-limiting circuits generally comprise diode bridge circuits, hot carrier diode circuits, germanium diode circuits or silicon diode circuits. Diode bridge circuits do not adequately protect the patient from shunt currents that occur in long leads because these circuits, by reason of their spatial requirements or bulk, are generally located in the biomedical equipment itself and away from the patient. For example, these circuits often require space to accommodate both a positive and a negative voltage source and at least four connecting leads, a signal source lead, a signal output lead and two voltage source leads.

Hot carrier diode circuits provide decreased shock protection as temperature increases. For example, the conductivity of these circuits increases by a factor of 14 (i.e., increases to fourteen times its original value) for each 25° C increase in temperature. Furthermore, hot carrier diode circuits inadequately limit the amount of current flowing to a patient. Typically, these circuits permit as much as 5 milliamps per lead, or 60 milliamps via a typical configuration of twelve leads, to pass to the patient.

Germanium diode circuits often have a low breakdown voltage that is inadequate to protect the patient when line voltages of 220 volts or higher are applied. Also, because the reverse leakage current of germanium diodes is relatively high, typically from one to twenty microamperes at room temperature, and doubles every 8° C above room temperature, the shock protection afforded to patients by this type of circuit decreases by 50 percent each time the temperature rises 8° C. The cause of a rise in temperature may be, for example, the hot lights or other heat sources in an operating room near to the circuit.

Silicon diode circuits have a high series resistance and low conductivity due to their small reverse leakage current. Because a patient's physiological signals are typically low amplitude signals requiring for conduction a device with high conductivity, the high-resistance low-conductivity characteristic of silicon diode circuits makes these circuits unsuited to conducting these signals.

SUMMARY OF THE INVENTION

According to the illustrated embodiment of the present invention, an optically excited diode current limiter circuit is placed in series with a lead having an electrode attached to a patient. The circuit conducts the patient's physiological signals picked up by the electrode while limiting the amount of current flowing through the lead so as to protect the patient from electrical shock.

The circuit includes two optically excitable silicon diodes connected back to back to each other, in series with the lead. One diode is connected to the patient electrode for receiving input signals picked up from the patient. The other diode is connected to a signal processing device for outputting patient signals to the device. The circuit also includes a variable light source for illuminating the diode junctions thereby to increase the reverse leakage current and, hence, the conductivity of the diodes, and an enclosure which prevents external light from reaching the diodes. As the intensity of the light source is increased, the conductivity of the diodes is increased sufficiently to allow small signal currents, below a predetermined level not hazardous to the patient, to pass through the diodes. Currents above this level are blocked by one of the diodes when flowing to the patient and by the other diode when flowing from the patient.

DESCRIPTION OF THE PREFERRED EMBODIMENT

Figure 1:
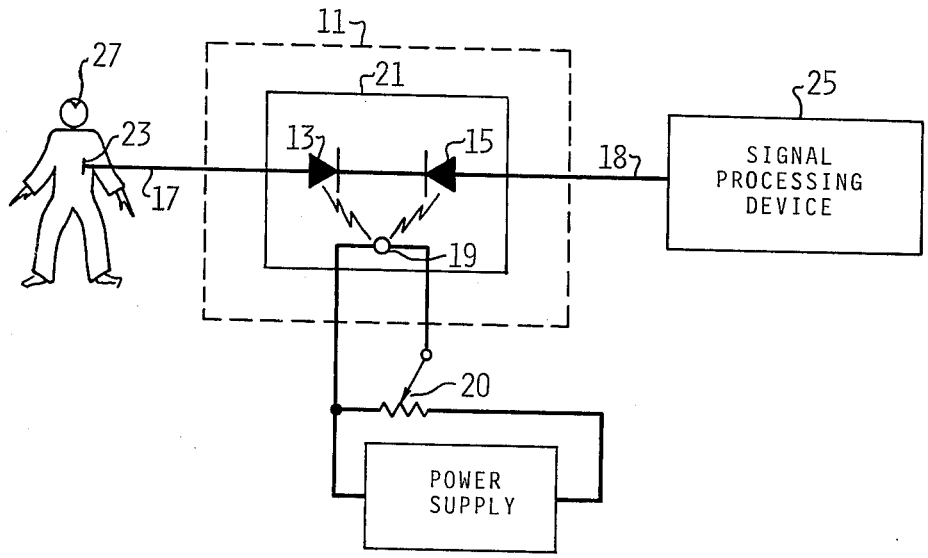
FIG. 1 is a diagrammatic illustration of one embodiment of the current limiter of the present invention.

FIG. 1 shows an optically excitable diode current limiter 11 having back to back silicon diodes 13, 15 connected in series with a lead 17, and having a variable light source 19 such as a potentiometer 20 controlled light source for optically exciting the diodes 13, 15, and an enclosure 21 to prevent external ambient light from reaching the diodes 13, 15. The light source may also be a light-emitting terminus such as the end of a fiber optic, or a light source that emits non-visible light such as X-rays. Signals picked up by an electrode 23 at the end of the lead 17, are selectively transmitted by the current limiter 11 via lead 18 to a signal processing device 25 for processing. Device 25 may be any physiological signal processing device such as an electrocardiograph.

The current limiter 11 may be placed near to the electrode 23, for example within 6 inches of electrode 23. When so placed, lead 17 between the patient and the current limiter 11 is short, thereby eliminating the hazard of shunt currents that can arise from long leads between the patient and the current limiter.

Figure 2:
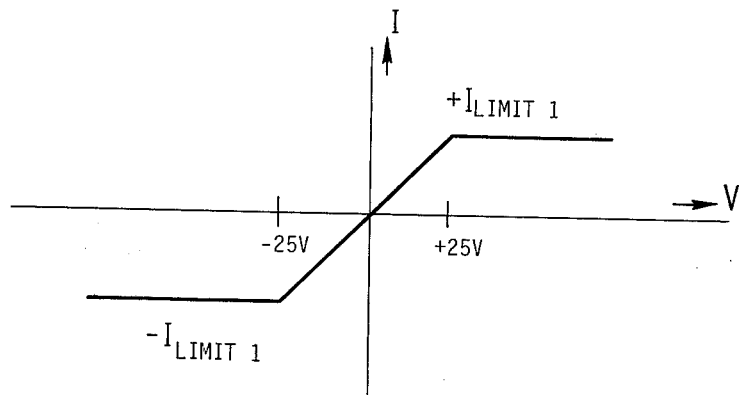
FIG. 2 is a waveform diagram illustrating the current-voltage characteristics of the current limiter of FIG. 1.
Figure 3:
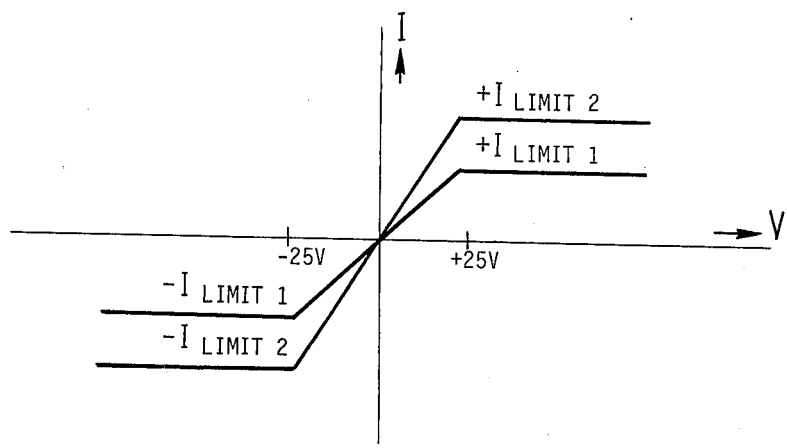
FIG. 3 is a waveform diagram illustrating the current-voltage characteristics of the current limiter of FIG. 1 when light from a varying light source is incident on the current limiter.

When light from the light source 19 is incident on the diodes 13, 15, which may be two diodes as shown in FIG. 1 or a greater number of diodes, free charge carriers are formed at the diode junctions. This reduces the resistance of the diodes 13, 15 to current flow. When small signals with voltage levels in the range from −25 millivolts to +25 millivolts are applied to the diodes the diodes 13, 15 act much like two resistors with a constant value producing a linear signal voltage-current relationship over this voltage range. When acting like resistors, the diodes conduct signals with small, non-hazardous currents such as physiological signal currents. FIG. 2 shows the relationship between applied voltages (V) and current flow (I) through the diodes 13, 15. For a selected amount of light incident on the diodes, 13, 15, the magnitude of the current conducted by the diodes 13, 15 varies linearly from $-I_{LIMIT_1}$ to $I_{LIMIT_1}$ as the applied voltage varies from −25 millivolts to +25 millivolts. As explained below, $I_{LIMIT_1}$ represents the reverse leakage current of the diodes, 13, 15 and is the maximum magnitude of current that can flow serially through both diodes 13, 15, for a selected amount of incident light. FIG. 3 shows that as the light source 19 is varied, for example by varying the potentiometer 20 thereby increasing the intensity of light incident upon the diodes 13, 15, $I_{LIMIT_1}$ increases in magnitude to another limiting value $I_{LIMIT_2}$.

The diodes 13, 15 conduct small currents flowing to or from the current limiter 11. The back to back orientation of the diodes has no appreciable effect on the direction of flow of such small currents when the diodes 13, 15 are acting like resistors. Consequently, a physiological signal flowing from a patient 27 to the current limiter 11 would not be blocked by diode 15; the current would be allowed to flow to the signal processing device 25.

However, as FIG. 2 shows, when the voltage of the applied signal is outside of the above-mentioned range, i.e., less than −25 millivolts or greater than +25 millivolts, the diodes 13, 15 act like typical diode semiconductors, each conducting current in one direction and blocking current greater in magnitude than $I_{LIMIT_1}$ flowing in an opposite direction. Signals having current levels greater in magnitude than $I_{LIMIT_1}$, for example, electrocautery, defibrillation, ground loops, stray capacitance or other signals occasioned by equipment failure, are deemed hazardous to the patient and are blocked by the current limiter 11 from flowing to or from the patient, i.e., no current greater than $I_{LIMIT_1}$ in magnitude is allowed to pass the current limiter 11. Diode 15 of the current limiter 11 blocks currents of hazardous signals that flow from diode 13 to diode 15. Diode 13 blocks currents of hazardous signal that flow from diode 15 to diode 13. A hazardous signal applied to diode 15 reverse biases diode 15. This causes diode 15 to conduct signals with current levels less than or equal to $I_{LIMIT_1}$ in magnitude, and to block or not conduct signals with current levels greater than $I_{LIMIT_1}$ in magnitude. Similarly, a hazardous signal applied to diode 13 reverse biases diode 13, thereby blocking the passage of all currents greater than $I_{LIMIT_1}$ in magnitude and permitting the flow of currents less than or equal to $I_{LIMIT_1}$ in magnitude.

I claim:

1. An apparatus for controlling the passage of electrical signals to and from a patient along a lead connecting the patient to a signal processing device, said apparatus comprising:
   a first unidirectional current limiter means having an optically excitable portion connected in series with said lead for conducting signals from said patient and blocking signals above a predetermined level to said patient;
   a second unidirectional current limiter means having an optically excitable portion connected in series to said first current limiter means and to said lead for conducting signals to said patient and blocking signals above a predetermined level from said patient;
   a light source disposed at a selected distance from said first and second current limiter means for illuminating the optically excitable portions of both of said current limiter means; and
   an enclosure placed around said first and second current limiter means and said light source for preventing external light from illuminating said first and second current limiter means.

2. The apparatus as in claim 1 wherein said first unidirectional current limiter means is an optically excitable silicon diode.

3. The apparatus as in claim 2 wherein said second unidirectional current limiter means is an optically excitable silicon diode.

4. The apparatus as in claim 3 wherein said light source is a variable light source for illuminating said first and second current limiter means with light of selected intensities.

* * * * *